United States Patent [19]

Courteille et al.

[11] Patent Number: 5,384,124
[45] Date of Patent: Jan. 24, 1995

[54] SOLID POROUS UNITARY FORM COMPRISING MICRO-PARTICLES AND/OR NANO-PARTICLES, AND ITS PREPARATION

[75] Inventors: Frederic Courteille, Cachan; Anne Coutel, Antony; Guy Lebreton, Gif-Sur-Yvette; Michel Veillard, Sceaux, all of France

[73] Assignee: Farmalyoc, France

[21] Appl. No.: 835,012

[22] Filed: Feb. 12, 1992

Related U.S. Application Data

[63] Continuation of Ser. No. 382,286, Jul. 20, 1989, abandoned.

[30] Foreign Application Priority Data

Jul. 21, 1988 [FR] France ................... 8809864

[51] Int. Cl.⁶ .................. A61F 6/06; A61K 9/22; A61K 9/62; B01J 13/04
[52] U.S. Cl. .................... 424/430; 34/284; 424/7.1; 424/436; 424/461; 424/462; 424/486; 424/499; 424/501; 427/213.31; 427/213.36; 428/402.24; 514/963; 514/965; 514/966; 514/967; 514/974
[58] Field of Search ............ 427/213.31, 213.36; 428/402.24; 424/461, 462, 486, 499, 501, 7.1, 430, 436; 514/963, 965, 974; 34/5, 284

[56] References Cited

U.S. PATENT DOCUMENTS

| | | | |
|---|---|---|---|
| 3,622,257 | 11/1971 | Hein et al. | 431/51 |
| 3,767,807 | 10/1973 | Blonde et al. | 514/474 |
| 3,772,430 | 11/1973 | Blonde et al. | 424/44 |
| 3,778,510 | 11/1973 | Blonde et al. | 424/553 |
| 4,247,406 | 1/1981 | Widder et al. | 424/486 X |
| 4,305,502 | 12/1981 | Gregory et al. | 34/5 X |
| 4,613,500 | 9/1986 | Suzuki et al. | 424/85.2 X |
| 4,693,912 | 9/1987 | Spadaro et al. | 427/213.3 |
| 4,698,264 | 10/1987 | Steinke | 428/402.24 X |
| 4,780,318 | 10/1988 | Appelgren et al. | 424/469 |
| 4,818,542 | 4/1989 | DeLuca et al. | 428/402.24 X |
| 4,936,901 | 6/1990 | Surgant, Sr. et al. | 504/133 |

FOREIGN PATENT DOCUMENTS

| | | |
|---|---|---|
| 284249 | 9/1988 | European Pat. Off. . |
| 0011839 | 3/1971 | Japan .................. 424/501 |
| 1216349 | 12/1970 | United Kingdom ........ 424/490 |
| 2192128 | 1/1988 | United Kingdom . |
| 8606626 | 11/1986 | WIPO . |

OTHER PUBLICATIONS

Chemical Abstracts, vol. 94, No. 24, 15 Jun. 1981, p. 346, No. 197440p.

*Primary Examiner*—Richard D. Lovering
*Attorney, Agent, or Firm*—Morgan & Finnegan

[57] ABSTRACT

New solid, porous unitary form comprising micro-particles and/or nano-particles, made by lyophilization are useful for the administration of therapeutically active substances, nutrition agents, diagnostic agents or cosmetic agents.

17 Claims, No Drawings

SOLID POROUS UNITARY FORM COMPRISING MICRO-PARTICLES AND/OR NANO-PARTICLES, AND ITS PREPARATION

This is a continuation of co-pending application Ser. No. 07/382,286, filed on Jul. 20, 1989, now abandoned.

FIELD OF THE INVENTION

The present invention provides to a new solid, porous unitary form, comprising micro-particles or nano-particles, of an active principle, and a process for its preparation.

BACKGROUND OF THE INVENTION

The preparation of micro-particles and nano-particles is principally used to retard dissolution of active principles, and, because of this finds, numerous applications in the field of controlled-release medicaments as well as in the field of taste-masking of medicaments intended for oral administration. It has, nevertheless, always been difficult to make a satisfactory formulation containing micro-particles or nano-particles in the form of unitary doses, and in particular a suitable formulation for oral administration.

In effect, industrial preparation of tablets and capsules requires flow and/or cohesion qualities of the granulated product which is to be divided, which micro-particles and/or nano-particles do not necessarily possess.

Tablets pose problems of integrity of the micro-particles and/or the nano-particles under the effect of compression; their slow disintegration speed does not always allow administration after disintegration and suspension in a glass of water.

Capsules do not always permit dispersion of the particles in the gastro-intestinal tract.

In addition, both capsules and tablets pose swallowing problems, which are particularly marked in the young and the old.

Finally, sachets are a pharmaceutically costly form which is not suitable for ambulatory use, and the dry-syrup form is not often feasible because of the premature liberation of the active principle from the micro-particles and/or nano-particles, or because of the physical and/or chemical stability of the preparation.

French Patents 2,036,890 and 2,366,835 describe pharmaceutical forms having the characteristic of dissolving or disintegrating rapidly in an aqueous medium or in saliva.

It has now been found that techniques having totally opposed objectives, such as delay of dissolution of an active principle on the one hand, and rapid disintegration or dissolution of the pharmaceutical form on the other hand, can be combined in a novel lyophilized unitary form, which is able to disintegrate easily and rapidly in water, which contains micro-particles and/or nano-particles, and in which settling and/or rising to the surface of the said particles during lyophilization has been avoided.

DESCRIPTION OF THE INVENTION

According to the invention, the new solid porous unitary form is made by a process which comprises forming a paste comprising i) micro-(and/or nano-)particles containing a predetermined quantity of one or more active principles, ii) at least one thickening or binding agent and/or extender, iii) one or more stabilizing agents to prevent settling and/or rising to the surface of the micro-(and/or nano-)particles, iv) optionally one or more other active principles or mixtures of micro-(and/or nano-)particles containing an active principle, and v) a suitable quantity of water so as to adjust the viscosity of the composition, and lyophilizing the paste obtained, preferably after it has been filled into suitable cavities.

The lyophilized product obtained can be mechanically divided into unitary doses having a well defined shape and volume, but it is preferable to distribute the paste in cavities of predetermined shape and size before the lyophilization operation. The quantity of the active principle(s) in the paste, and the shape and the size of the cavities is calculated so as to obtain a precisely defined quantity of the active principle(s) in each unitary dose.

In the above description, as well as in that which will follow, the term "active principle" means any substance containing at least one therapeutically active product, one nutrition agent, one diagnostic agent or one cosmetic agent, it being possible for the latter to be combined with one or more other substances of the same type or to be combined with other micro-(or nano-)particles themselves containing other substances mentioned above.

According to a feature of the invention, any particle with a diameter of between 1 $\mu$ and 2 mm is called a micro-particle. These micro-particles may be micro-spheres, extrudates, micro-capsules or micro-granules allowing retention of an active principle and thus avoiding it becoming available completely and immediately by simple contact with aqueous liquid media. Any particle with a diameter of less than 1 $\mu$ is called a nano-particle. These nano-particles may be nano-spheres or nano-capsules, and have characteristics of retention of the active principle of the same nature as micro-particles, it being understood that because of their small size, they are able to cross the epithelium of the intestinal mucosa, and should therefore preferably be constituted of bioresorbable polymers.

The mixture of micro-(or nano-)particles is prepared by any known method employing the use of a polymer or a macromolecular substance. More particularly, the techniques of micro-encapsulation by solvent evaporation, micro-encapsulation by coacervation, micro-encapsulation by turbine-coating or by assembly and turbine-coating, simple extrusion, extrusion-spheroidization, extrusion-spheroidization and coating, or air-fluidized bed coating may be used.

The implementation of the these methods is mentioned in more detail in the references given below as examples:

French Patent Application 2,484,281

T. M. Serajuddin et al., J. Pharm. Sci., 73 (9), 1203 (1984)

L. Luzzi et al., Biochemical Applications of Micro-encapsulation, CRC Press, Franklin. Lim Editor (1984), chap. 1, pages 1 to 19

A.-C. Vial-Bernasconi et al., S.T.P. Pharma, 4 (5), 397 (1988)

European Patent Application EP 204 596

F. Briquet et al., S.T.P. Pharma, 2 (22), 986 (1986)

N. Sarisuta et al., Drug development and industrial pharmacy, 14 (5), 683 (1988)

European Patent Application EP 193,208

French Patent Application FR 2,608,988

Encyclopedia of polymer science and engineering, vol. 9, 2nd ed., John Wiley and Sons Inc. (1987), pages 724 to 745

Theory and Practice of Industrial Pharmacy, 2nd ed., L. Lachman, H. A. Lieberman and J. L. Kanig, Ed. Lea and Febiger, Philadelphia (1976), pages 420 to 465

Formes Pharmaceutiques Nouvelles—Aspects Technologique, Biopharmaceutique et Médical [New pharmaceutical forms—technological, biopharmaceutical and medical aspects], Lavoisier Tech. et Doc., P. Buri, F. Puisieux, E. Doelker and J. P. Benoit, Chap. XV, page 613 (1985).

It is understood that the polymers or the macromolecular substances which are capable of being used are not limited to those which are mentioned in the above methods. Other polymers or macromolecular substances, if necessary pharmaceutically acceptable, may also be used. For example the derivatives of cellulose (cellulose, carboxymethylcellulose, cellulose acetophthalate, methylcellulose, ethylcellulose, hydroxyethylcellulose, hydroxypropylcellulose, hydroxypropylmethylcellulose and hydroxymethylcellulose phthalate for example), acrylic derivatives (polymethacrylate, polyacrylamide, polyacryldextran and polyalkylcyanoacrylate for example), alginic acid, dextran, gelatin, polyethylene glycol, polyvinylalcohol, propylene glycol alginate, starch, zein, sucrose, polyacetal, polyglycolic-polylactic acid, polyhydroxybutyric acid, polyamide, polyanhydride, poly-ε-caprolactone, polydimethylsiloxane, polyorganophosphazene, polyorthoesters, polyamino-acids, polyvinylpyrrolidone, chitin and its derivatives, collagen, polyglutaraldehyde, polypropylene, polytetrafluoroethylene, polyethylene, polyvinyl chloride and polyurethanes may in particular be used.

Thickening and binding agents, which serve as a support, are understood to include any water-soluble or water-dispersible substance, which allows cohesion of the mass to be ensured, and is if necessary acceptable from a pharmaceutical point of view and inert with respect to the active principle. These substances are in particular chosen from polypeptides such as gelatin or partly hydrolyzed gelatin, colloids, high molecular weight polysaccharides, high polymers capable of giving colloidal solutions, for example natural gums (e.g. gum arabic, and gum tragacanth) synthetic or semi-synthetic gums (e.g. glycosylglucans, and xanthan gums), dextran, dextrin, alginates (sodium alginate), pectinates, cellulose derivatives (e.g. microcrystalline cellulose, and carboxymethylcellulose), water-dispersible starch derivatives, colloidal silicas, bentonites, or other support substances, such as polyvinyl alcohol, polyvinylpyrrolidone, polyethylene glycols (in particular PEG 20,000 and PEG 6,000), acrylic polymers or copolymers, and even mixtures of such substances as those mentioned above. Preferably, a water-soluble substance is used. By "extenders" are designated substances, preferably soluble and crystallizable, and if necessary pharmaceutically acceptable, which improve the physical properties of the new unitary form. These substances may in particular be chosen from lactose, glycine, sorbitol, mannitol, glucose or maltodextrins, or even, optionally, from oxides (magnesium oxide), carbonates (calcium carbonate), phosphates (tricalcium phosphate) or micro-crystalline cellulose, or mixtures of these substances.

It is understood that the paste intended for lyophilization must necessarily contain at least one substance chosen from the thickening substances and the extenders mentioned above, but it is equally advantageous to use one or more thickening substances and one or more extenders at the same time.

The thickening and binding substances and the extenders are chosen so as to confer on the paste to be lyophilized a rheological behaviour and a viscosity which are adapted to a good division of the product and to maintenance of the various components in suspension (flow, homogeneity, repeatability of the divided volume, stability of the suspension during division). These substances are also chosen so as to ensure the correct texture of the final lyophilized product (for example sufficient hardness to allow extrusion through a blister).

The paste intended for lyophilization must, in addition, contain one or more suspension agents intended to prevent sedimentation of the micro-(or nano-)particles during lyophilization. These stabilizing agents are solid particulate substances of micronic size, which are inert with respect to the mixture. They can either be insoluble, or soluble and in excess with respect to the solubilizing power of the paste to be lyophilized. They are chosen so that their sedimentation rate is of the same order of magnitude as that of the micro-(or nano-)particles. Because of this, the choice of stabilizing agent is modified as a function of the density and size of the micro-(or nano-)particles as well as the pH conditions of the solution into which it is introduced. Among suitable stabilizing agents oxides (titanium oxide, magnesium oxide, iron oxides and silica for example), salts such as carbonates (calcium carbonate and magnesium carbonate for example), silicates (kaolin for example), phosphates (tricalcium phosphate for example) and sugars (lactose, glucose, mannitol, laevulose and maltodextrin for example) may be mentioned.

In the case of nano-particles having a density close to that of the aqueous phase of the paste to be lyophilized, this additive may prove not to be indispensible.

In the process according to the invention, it is understood that the order of introduction of the different substances depends on the substances themselves, certain of them being capable of being mixed previously.

Generally, the thickening and binding substances constitute from 0.01 to 99% by weight with respect to the dry mass of the lyophilizate. It is also possible to introduce only extenders, and not to employ any thickening substance.

The extenders are generally in excess with respect to the solubilizing power of the paste to be lyophilized. They constitute 1 to 99% by weight with respect to the total dry mass of the lyophilizate. It is, however, possible to introduce only thickening substance, without using extenders.

The stabilizing agent is a function of particles which will constitute the paste to be lyophilized, and represents from 1 to 70% by weight with respect to the dry lyophilized mass.

The quantity of water introduced is determined in such a manner that the paste to be lyophilized has a suitable rheological behaviour and viscosity. It is, in fact, desirable to adjust the viscosity of the paste to be lyophilized so that it is sufficiently fluid to allow of regular division, and sufficiently viscous to avoid sedimentation of the micro-(and/or nano-)particles.

The quantity of water introduced into the constitution of the mixture can represent 10 to 90% by weight with respect to the wet mass to be lyophilized, varying with the nature of the substances chosen to constitute the mixture.

Lastly, the mixture of particles containing the active principle(s) is prepared in such a way that the polymer or the macromolecular substance introduced represents 0.1 to 80% by weight with respect to the dry mass of the lyophilizate.

In addition, the preparation intended to be lyophilized may optionally contain other additives, such as, for example, surfactants, or other substances which are compatible, and if necessary pharmaceutically acceptable, such as colorants, sweetening or taste modifying substances, preservatives or any other substance which is compatible with the rest of the mixture.

As an example, the surfactants may be chosen from the non-ionic agents [polyoxyethylene polysorbates (Tween), sorbitan esters (Span), copolymers of ethylene oxide and propylene, polyoxyethyleneglycol ethers and fatty acid ethers], anionic agents (sulphosuccinic acid esters: dialkylsulphosuccinates, for example sodium dioctylsulphosuccinate), and cationic agents (quaternary ammonium salts).

The sweetening or taste modifying substances may be in particular sucrose, glucose, xylose, sorbitol, saccharin, saccharinates, cyclamates, aspartame, ammonium glycyrrhizinate or again citric, ascorbic or tartaric acids, or any other substance normally used for taste modification in the food or pharmaceutical industry and which is compatible with the products with which it is present.

All these substances may equally well be added at the beginning, during or at the end of making up of the paste to be lyophilized.

It is understood that this new solid unitary form can be applied to the administration of many sorts of substances, and more specially to pharmaceutically active principles which are usable orally and which are intended both for human medicine and for veterinary medicine. It is also applied to nutrition agents, to diagnostic agents and to cosmetic agents.

For example, among the pharmaceutically active substances which are administrable in this form there may be mentioned antibiotics (e.g. spiramycin, pristinamycins, tetracyclines, metronidazole, pefloxacine and derivatives of the quinolone family, cefixime and josamycine), anti-inflammatories and anti-rheumatics (e.g. ketoprofen), analgesics (e.g. aspirin, paracetamol and clometacin), tranquilizers (e.g. lorazepam, oxazepam, zopiclone and other derivatives of the cyclopyrrolone family and derivatives of the phenothiazine family), cardiovascular agents and cerebral vasodilators (e.g. isosorbide dinitrate, trinitrin, dihydroergotoxine, digoxin, quinacainol, propranolol, oxoprenolol, vincamine and nicergoline), cerebral protectors (gangliosides for example), antispasmodics and antisecretories, anti-asthmatics, therapeutic agents for diseases of the gastro-intestinal tract, hepatic protectors, hormones, contraceptives, medicaments intended for the treatment of allergies, vaccines, vitamins or even peptides, polypeptides or proteins.

Among the nutrition agents the amino acids may be mentioned in particular, for example, methionine, lysine and carnitine lysinate.

The new solid unitary form may also be applied to in vitro diagnostic agents, for example acridine orange (phagocytosis marker), or to in vivo diagnostic agents.

When the new solid unitary form is applied to cosmetic agents, the active principle may be in particular a breath-modifying substance such as, for example, menthol or mint or eucalyptus essences.

The quantity of active principle introduced is variable as a function of its nature, but it must be understood that this new solid form can allow unitary doses with a high content of active principle to be prepared, thus allowing the multiplicity of doses to be reduced because of the controlled liberation of the active principle. Generally, the quantity of active principle can be up to 95% by weight with respect to the dry substance.

The new solid form according to the invention thus presents the advantage of combining a primary unitary form with very rapid disintegration in an aqueous medium, with a secondary form with a controlled dissolution composed of a micro-(and/or nano-)particulate system.

The primary form allows easier use, avoids, in particular, agglomeration of the particles, and, above all, has the advantage of containing a predetermined quantity of active principle.

The secondary form controls liberation of the active principle in contact with aqueous media. It is intended most particularly for substances which are unstable in solution. For example, when the active principle is intended for oral administration, the form of micro-(and/or nano-)particles allows controlled release of the active principle; the substance is protected until it reaches the required area or the chosen moment. The liberation of the active substance is therefore linked to factors such as pH, ionic strength, the presence of an enzyme or the presence or absence of a specific bacterial flora. The choice of size of the micro-(and/or nano-)particles allows the speed of liberation of the active principle to be predetermined; for example the speed of liberation in the gastro-intestinal environment when the active principle is administered orally. This secondary form can, of course, contain several series of micro-(or nano-)particles, either mixed with each other and from which the active substances will be simultaneously or successively liberated, or contained one within the other and from which the active substances will be successively liberated. The secondary form also allows the taste of the active substances, for example of bitter products, to be masked.

The new solid unitary form according to the invention, when applied to pharmaceutical formulations, is, because of this, especially indicated for oral administration; but it can also be used for rectal or vaginal administration.

In view of its advantages, the new solid unitary form according to the invention is especially indicated for oral pharmaceutical formulations intended for paediatrics or geriatrics, for formulations for buccal bioadhesion such as, for example, breath freshening systems, for formulations intended for treatment of the colon, or even in veterinary medicine, in the case of foodstuff adjuvants or medical diagnostics.

EXAMPLES

The following Examples illustrate the present invention.

EXAMPLE 1

Preparation of a lyophilizate containing micro-spheres of spiramycin 50 to 400 μ in diameter:

a) Spiramycin base (33 g) and Eudragit E 100 (27 g) are dissolved in dichloromethane (100 cc). The solution obtained is called solution A.

b) Polyvinyl alcohol (Mowiol 8.88 from Hoechst) (14 g), spiramycin base (3 g) and sodium chloride (70 g) are dissolved in water (700 cc). The solution obtained is called solution B.

c) Solution A is dispersed in solution B with mechanical stirring. Stirring is maintained until the organic solvent is eliminated, that is 10 hours at ambient temperature.

d) The micro-spheres obtained are filtered, washed and dried (50 g dry substance). A pale yellow powder with an insipid flavor is thus obtained. Examination with a microscope reveals individual spherical micro-particles 50 to 400 μ in diameter. Their spiramycin content is about 55%.

e) The spiramycin micro-spheres obtained previously are mixed dry with mannitol (46 g) and titanium oxide (17 g).

f) A fluid gel is prepared by dissolving xanthan gum (85 mg), dextran 70 (5 g) and sodium dioctylsulphosuccinate (250 mg) in water (76 cc).

g) This fluid gel is added to the mixture of powders prepared at e), and the mixture is stirred under reduced pressure (about 0.1 bar). A paste with relative viscosity of about 685 mPa.s at a shear gradient of 44 $s^{-1}$ (coaxial viscometer) is obtained.

h) The paste is distributed into 1.2 cc transparent polyvinyl chloride cavities at a rate of 1,150±57.5 mg. per cavity.

i) The paste is frozen to −25° C. in a lyophilizer, and then lyophilized for 5 hours; the temperature of the product changes from −25° to +40° C. The cavities are thermosealed with a sheet of aluminium-polyvinyl chloride-polyvinyl dichloride complex.

The lyophilizate obtained contains 750,000 IU spiramycin per cavity. Its flavor is insipid. Its mechanical resistance allows each unit to be pushed out of the thermoformed blister pack and handled until the moment of administration.

The disintegration time in water of the lyophilizate varies from 1 to 3 minutes. The micro-spheres do not liberate spiramycin in a glass of water after 15 minutes; they liberate spiramycin in media of pH less than 5, such as gastric juice for example.

EXAMPLE 2

The preparation of micro-spheres of spiramycin is carried out as in Example 1 from a) to d).

e) The previously obtained micro-spheres of spiramycin are mixed dry with mannitol (46 g), titanium oxide (8.5 g) and calcium carbonate (8.5 g).

A fluid gel is prepared as described in Example 1 f), and added to the mixture of powders prepared at e). The paste obtained is distributed into cavities and lyophilized as described above in Example 1.

EXAMPLE 3

The preparation of micro-spheres of spiramycin is carried out as in Example 1 from a) to d).

e) The previously obtained micro-spheres of spiramycin are mixed dry with mannitol (46 g), titanium oxide (8.5 g) and tricalcium phosphate (8.5 g).

A fluid gel is prepared as described in Example 1 f), and added to the mixture of powders prepared at e). The paste obtained is distributed into cavities and lyophilized as described above in Example 1.

EXAMPLE 4

The preparation of micro-spheres of spiramycin is carried out as in Example 1 from a) to d).

e) The previously obtained micro-spheres of spiramycin are mixed dry with mannitol (46 g), titanium oxide (8.5 g) and kaolin (8.5 g).

A fluid gel is prepared as described in Example 1 f), and added to the mixture of powders prepared at e). The paste obtained is distributed into cavities and lyophilized as described above in Example 1.

EXAMPLE 5

The preparation of micro-spheres of spiramycin is carried out as in Example 1 from a) to d).

e) The previously obtained micro-spheres of spiramycin are mixed dry with mannitol (46 g) and tricalcium phosphate (17 g).

A fluid gel is prepared as described in Example 1 f), and added to the mixture of powders prepared at e). The paste obtained is distributed into cavities and lyophilized as described above in Example 1.

EXAMPLE 6

The preparation of micro-spheres of spiramycin is carried out as in Example 1 from a) to d).

e) The previously obtained micro-spheres of spiramycin are mixed dry with mannitol (46 g) and kaolin (17 g).

A fluid gel is prepared as described in Example 1 f), and added to the mixture of powders prepared at e). The paste obtained is distributed into cavities and lyophilized as described above in Example 1.

EXAMPLE 7

Preparation of a lyophilizate containing micro-spheres of spiramycin 50 to 150 μ in diameter.

a) Spiramycin base (66.6 g) and ethylcellulose (N 100 quality from Hercules) (33.4 g) are dissolved in dichloromethane (700 cc). The solution obtained is called solution A.

b) Polyvinyl alcohol (Mowiol 8.88 from Hoechst) (45 g), spiramycin base (9.5 g) and sodium chloride (225 g) are dissolved in water (2,100 cc). The solution obtained is called solution B.

c) Solution A is dispersed in solution B under constant mechanical stirring (350 rev/min) and stirring is continued until the organic solvent is eliminated, that is 18 hours at ambient temperature.

d) The fractions greater than 150 μ and less than 50 μ are removed by wet sieving. The 50–150 μ fraction is washed and dried. A pale yellow powder (72.5 g) is obtained which is constituted of individual spherical micro-spheres from 50 to 150 μ in diameter. Their flavor is insipid. Their spiramycin content is about 66.7%.

e) The previously obtained micro-spheres of spiramycin are mixed dry with mannitol (130 g) and titanium oxide (15 g).

f) A fluid gel is prepared by dissolving xanthan gum (40 mg), dextran 70 (2.9 g) and sodium dioctylsulphosuccinate (73 mg) in water (135 cc).

g) This fluid gel is added to the mixture of powders prepared at e), and the mixture is stirred under reduced pressure (about 0.1 bar).

h) The paste is distributed into 1.2 cc transparent polyvinyl chloride cavities at the rate of 1,200 mg.

i) The paste is frozen to −25° C. in a lyophilizer, then lyophilized for 5 hours; the temperature of the product goes from −25° C. to +40° C. The cavities are thermosealed with a sheet of an aluminium-polyvinyl chloride-polyvinyl dichloride complex.

The lyophilizate obtained contains 750,000 IU of spiramycin per cavity. Its flavor is insipid. Its mechanical resistance allows pushing out of the cavities of the thermoformed blister pack and handling until the moment of administration.

The disintegration time of the lyophilizate varies in water from 15 to 30 seconds. The micro-spheres do not liberate spiramycin in a glass of water after 15 minutes; they liberate spiramycin in media with pH less than 5, such as gastric juice for example.

EXAMPLE 8

Preparation of a lyophilizate containing nano-spheres of acridine orange 100 to 200 nm in diameter. Acridine orange is used in this example for the purposes of in vitro diagnosis of phagocytosis of nano-particles by macrophages.

a) Acridine orange (0.001 g) and poly-(DL lactic acid) (PLA 50, molecular mass 49,000, from Rhône-Poulenc) (0.5 g) are dissolved in acetone (100 cc). The solution obtained is called solution A.

b) A mixed polymer of ethylene oxide and propyleneglycol (Pluronic F 68 ® or Poloxamer 188 ®)(0.5 g) is dissolved in distilled water (200 cc). The solution obtained is called solution B.

c) Solution A is emulsified in solution B by stirring with a magnetized bar at a speed of 100 rev/min.

d) Stirring is maintained for 24 hours at ambient temperature and atmospheric pressure in order to remove the acetone by evaporation.

e) The suspension obtained is filtered on a filter of porosity 0.8 μ.

f) It is centrifuged at 10,000 rev/min for 1 hour, then 155 cc of supernatant is removed. A sediment of nano-spheres of acridine orange (about 0.5 g) is thus obtained, which is redispersible in the remaining aqueous phase (45 cc). Examination with a microscope reveals individual and spherical nano-particles from 100 to 300 nm in diameter. Their acridine orange content is about 0.2%.

g) The previously obtained sediment of nano-spheres is again dispersed in the remaining aqueous phase (45 cc). Xanthan gum (Rhodigel 23 from Rhône-Poulenc) (12.5 mg) and dextran 70 (1 g) are added and the mixture is stirred until a fluid gel is obtained.

h) Titanium oxide (10 g) is mixed dry with mannitol (62 g).

i) The fluid gel prepared at g) is added to the mixture of powders prepared at h), and the mixture is stirred under reduced pressure (about 0.1 bar).

j) The paste is distributed into 1.2 cc transparent polyvinyl chloride cavities at the rate of 1,200 mg.

k) The paste is frozen to −25° C. in a lyophilizer, then lyophilized for 5 hours; the temperature of the product changes from −25° to +40° C. The cavities are thermosealed with a sheet of an aluminium-polyvinyl chloride-polyvinyl dichloride complex.

The lyophilizate obtained contains about 0.01 mg acridine orange per cavity. Its mechanical resistance allows pushing out of the cavities of the thermoformed blister pack and handling until the moment of administration.

The disintegration time in water of the lyophilizate is less than 1 minute.

EXAMPLE 9

Preparation of a lyophilizate containing micro-granules of paracetamol from 0.8 to 1.6 mm in diameter.

a) Paracetamol (powdered quality, Rhône-Poulenc) (182 g) is mixed dry with microcrystalline cellulose (Avicel PH 101 quality from FMC Corp.) (728 g).

b) The preceding mixture is wetted with a 1.5% aqueous solution of sodium carboxymethylcellulose (6 l).

c) The wet mass is extruded through a 1 mm grid then spheroidized for about 5 minutes.

d) It is dried in an oven at 35° C.

e) The fraction of diameter between 1 and 1.5 mm is selected by sieving. About 900 g of spherical uncoated micro-granules of paracetamol are obtained, of size of between 1 and 1.5 mm (yield about 90%).

f) The solution below (1,800 g) is sprayed onto the micro-granules (900 g) obtained at e) in an air-fluidized bed device:

| | |
|---|---|
| Ethylcellulose 30% aqueous dispersion (Aquacoat EDC 30 from FMC Corp.) | 50.0 g |
| Diethyl phthalate | 3.0 g |
| Yellow iron oxide | 0.4 g |
| Distilled water | 46.6 g |

About 1 kg of prolonged-liberation micro-granules of paracetamol are obtained, of diameter between 0.8 and 1.6 mm and of a brown color. Their paracetamol content is about 15.2%.

g) 110 g of the coated micro-granules of paracetamol obtained previously at f) are mixed dry with mannitol (96 g) and titanium oxide (33 g).

h) A fluid gel is prepared by dissolving xanthan gum (Rhodigel 23 from Rhône-Poulenc) (500 mg), sodium dioctylsulphosuccinate (500 mg) and dextran 70 (10 g) in water (150 cc).

i) This fluid gel is added to the mixture of powders prepared in g), and the mixture is stirred under reduced pressure (about 0.1 bar).

j) The paste is distributed into 1.2 cc transparent polyvinyl chloride cavities, at the rate of 1,200 mg per cavity.

k) The paste is frozen to −25° C. in a lyophilizer, then lyophilized for 5 hours; the temperature of the product changes from −25° to +40° C. The cavities are thermo-sealed with a sheet of aluminium-polyvinyl chloride-polyvinyl dichloride complex.

The lyophilizate obtained contains 50 mg of paracetamol per cavity. Its mechanical resistance allows pushing out of the thermoformed blister pack and handling until the moment of administration.

The disintegration time of the lyophilizate in water varies from 1 to 3 minutes. The prolonged-liberation microgranules liberate practically no paracetamol during disintegration of the lyophilizate in aqueous media.

Liberation of the paracetamol from the microgranules is controlled by the polymeric membrane.

The in vitro dissolution kinetics of the paracetamol, measured by method No. 2 using a paddle, as described in USP XXI, are shown by the results collated in the attached table.

IN VITRO DISSOLUTION KINETICS OF
PARACETAMOL FROM COATED
PROLONGED-LIBERATION
MICRO-GRANULES OF PARACETAMOL (USP XXI method using paddle No. 2—37° C.—120 rev/min —pH 1 medium=0.1N HCl—pH 7.4 medium=disodium phosphate/citric acid buffer solution—read with UV spectrophotometer at 242 nm).

| DISSOLUTION ENVIRONMENT | TIME | PERCENTAGE DISSOLVED |
|---|---|---|
| pH 1 0.1 N HCl | 30 minutes | 3.5% |
| | 1 hour | 5.0% |
| | 2 hours | 8.5% |
| pH 7.4 buffer | 3 hours | 13.5% |
| | 4 hours | 17.5% |
| | 5 hours | 32.0% |
| | 6 hours | 50.5% |
| | 7 hours | 65.0% |
| | 8 hours | 77.5% |
| | 24 hours | 100.0% |

EXAMPLE 10

Preparation of an oral lyophilizate containing microspheres of ketoprofen.

a) Ketoprofen (60 g) and a mixture (9:1) of ethylcellulose/Eudragit RS 100 (240 g) are dissolved in dichloromethane (1.5 l) using a paddle stirrer (Heidolph) at 500 rev/min, b) a 0.27% (w/v) aqueous solution of Methocel K4M (1.5 l) is added to the preceding solution to obtain an emulsion, c) after evaporation of the dichloromethane under reduced pressure the micro-spheres are separated by centrifugation and washed with water (3 l), The micro-spheres are dried at ambient temperature for 2 to 3 hours in an air-fluidized bed apparatus, d) micro-spheres obtained as described above (500 mg) (containing 20.2% of active principle), are mixed dry with:

| | |
|---|---|
| xanthan gum (Rhodigel 23 from Rhône-Poulenc) | 0.75 mg |
| sodium dioctylsulphosuccinate | 0.38 mg |
| Dextran 70 | 30.00 mg |
| Lactose | 218.87 mg | then water (500 mg) is added e) the paste is distributed into polyvinyl chloride cavities, then lyophilized in the conditions described in the preceding examples.

The lyophilizate obtained contains 100 mg ketoprofen per cavity.

The disintegration time of the lyophilizate is 1 min 20 sec.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A solid, porous unitary form comprising a combination of a primary unitary form which disintegrates in aqueous medium and a secondary unitary form, the secondary unitary form having controlled dissolution and controlled release of an active principle contained in the secondary unitary form, said secondary unitary form comprising particles having a diameter up to 2 mm and containing a predetermined amount of one or more active principles, said solid, porous unitary form being obtained by A) forming a paste by mixing i) particles of the secondary unitary form, the particles having a diameter up to 2 mm and containing a predetermined quantity of at least one active principle;

ii) at least one thickening or binding agent and/or extender;

iii) at least one stabilizing agent to prevent settling and/or rising to the surface of the particles having a diameter up to 2 mm;

iv) optionally at least one other active principle or mixture of particles having a diameter up to 2 mm and containing an active principle; and v) water in an amount sufficient to adjust the viscosity of the paste such that the paste is sufficiently fluid to allow regular division and the paste is sufficiently viscous to avoid sedimentation of the particles, and B) lyophilizing the paste to obtain the solid, porous unitary form which is a combination of the primary unitary form and the secondary unitary form.

2. A unitary form according to claim 1 obtained by lyophilization of the paste after it has been distributed into cavities of predetermined shape and size.

3. A unitary form according to claim 1 divided into unitary doses of predetermined shape and volume.

4. An oral pharmaceutical formulation comprising a solid, porous unitary form according to claim 3.

5. A vaginal or rectal pharmaceutical formulation comprising a solid, porous unitary form according to claim 3.

6. A unitary form according to claim 1, in which the active principle is a therapeutically active substance.

7. A unitary form according to claim 1, in which the active principle is a nutrition agent, a diagnostic agent or a cosmetic agent.

8. A method of using unitary form according to claim 1, for veterinary use.

9. A unitary form according to claim 1, in which the said particles having a diameter up to 2 mm comprise, in addition to the active principle, a compatible polymer or other macromolecular substance.

10. A unitary form according to claim 1 wherein the thickening or binding agent is selected from the group consisting of a polypeptide, a high polymer capable of giving colloidal solutions, a cellulose derivative, and a water dispersible starch derivative.

11. A unitary form according to claim 1 wherein the extender is selected from the group consisting of lactose, glycine, sorbitol, mannitol, glucose, maltodextrin, an oxide, a carbonate, a phosphate, micro-crystalline cellulose, and mixtures thereof.

12. A unitary form according to claim 1 wherein the stabilizing agent is selected from the group consisting of an oxide, salts, and a sugars.

13. A solid, porous unitary form comprising a combination of a primary unitary form which disintegrates in aqueous medium and a secondary unitary form having controlled dissolution and controlled release of an active principle, said secondary unitary form comprising a particulate system having a diameter up to 2 mm, said solid, porous unitary form being obtained by A) forming a paste by mixing
  i) particles having a diameter up to 2 mm containing a predetermined quantity of at least one active principle;
  ii) at least one thickening or binding agent, wherein the thickening or binding agent is selected from the group consisting of a polypeptide, a high polymer capable of giving colloidal solutions, a cellulose derivative, and a water dispersible starch derivative; and/or extender, wherein the extender is selected from the group consisting of a lactose, glycine, sorbitol, mannitol, glucose, maltodextrin, an oxide, a carbonate, a phosphate, micro-crystalline cellulose and mixtures thereof;
  iii) at least one stabilizing agent to prevent settling and/or rising to the surface of the particles having a diameter up to 2 mm wherein the stabilizing agent is selected from the group consisting of an oxide, salts, and sugars;
  iv) optionally at least one other active principle or mixture of particles having a diameter up to 2 mm containing an active principle; and
  v) water, and B) lyophilizing said paste to obtain the solid, porous unitary form.

14. A process for the preparation of a solid, porous unitary form wherein the solid porous unitary form comprises a combination of a primary unitary form which disintegrates in aqueous medium and a secondary unitary form, the secondary unitary form having controlled dissolution and controlled release of an active principle contained in the secondary unitary form, said process comprising forming a paste comprising
  i) particles of the secondary unitary form, the particles having a diameter up to 2 mm and containing a predetermined quantity of one or more active principles;
  ii) at least one thickening or binding agent and/or extender;
  iii) one or more stabilizing agents to prevent settling and/or rising to the surface of the particles having a diameter up to 2 mm;
  iv) optionally one or more other active principles or mixtures of particles having a diameter up to 2 mm containing an active principle; and
  v) water in an amount sufficient to adjust the viscosity of the paste such that the paste is sufficiently fluid to allow regular division and the paste is sufficiently viscous to avoid sedimentation of the particles, and lyophilizing the paste to obtain the solid porous unitary form comprising the combination of the primary unitary form and the secondary unitary form.

15. Process according to claim 14 in which the paste obtained is lyophilized after it has been distributed into cavities of predetermined shape and size.

16. Process according to claim 14 in which the lyophilizate is divided into unitary doses of predetermined shape and volume.

17. Process according to claim 14 in which the said particles having a diameter up to 2 mm comprise, in addition to the active principle, a compatible polymer or other macromolecular substance.

* * * * *